United States Patent [19]
Bergman et al.

[11] Patent Number: 5,658,610
[45] Date of Patent: Aug. 19, 1997

[54] METHOD AND DEVICE IN HIGH-PRESSURE TREATMENT OF LIQUID SUBSTANCES

[75] Inventors: Carl Bergman; Jan Westerlund, both of Västerås, Sweden

[73] Assignee: ASEA Brown Boveri AB, Västerås, Sweden

[21] Appl. No.: 525,622

[22] PCT Filed: Mar. 23, 1994

[86] PCT No.: PCT/SE94/00260

§ 371 Date: Sep. 22, 1995

§ 102(e) Date: Sep. 22, 1995

[87] PCT Pub. No.: WO94/21145

PCT Pub. Date: Sep. 29, 1994

[30]   Foreign Application Priority Data

Mar. 25, 1993 [SE] Sweden ......................... 9300995

[51] Int. Cl.$^6$ ........................................... A23P 1/00
[52] U.S. Cl. ........................ 426/665; 99/467; 99/484; 426/416; 426/599
[58] Field of Search ........................... 426/599, 665, 426/416; 99/467, 484; 422/295, 296; 100/93 P

[56]   References Cited

U.S. PATENT DOCUMENTS 5,213,029  5/1993  Yutaka ........................... 99/484
5,328,703  7/1994  Nakagawa et al. ............. 426/599

FOREIGN PATENT DOCUMENTS 4242311  8/1993  Germany.

OTHER PUBLICATIONS

Patent Abstracts of Japan, vol. 16, No. 334, C–964, Japanese Publication No. 04–09673, "High–Pressure Liquid Processing Device", Inventors: Manabe Yuko et al., Applicant: Mitsubishi Heavy Ind Ltd., Published: Mar. 30, 1992.

*Primary Examiner*—George Yeung
*Attorney, Agent, or Firm*—Burns, Doane, Swecker & Mathis, L.L.P.

[57]   ABSTRACT

A method and device for high-pressure treatment of liquid substances, for example foodstuffs. The substance undergoes a cyclic process whereby a limited amount of the substance during each cycle is pressurized in a pressure intensifier (1) to a predetermined pressure and is then maintained at this pressure for a predetermined period of time. After the substance has been pressurized in the pressure intensifier (1), it is conducted to a pressure chamber (10) while maintaining the predetermined pressure. The substance is further caused to reside in the pressure chamber (10) for the predetermined period of time by being caused to pass over a predetermined distance between an inlet (9a) and an outlet (9b), which are arranged in the pressure chamber (10).

30 Claims, 3 Drawing Sheets

METHOD AND DEVICE IN HIGH-PRESSURE TREATMENT OF LIQUID SUBSTANCES

TECHNICAL FIELD

The present invention relates to a method and a device for high-pressure treatment of liquid substances, for example foodstuffs, wherein the substance undergoes a cyclic process where a limited amount of the substance during each cycle is pressurized in a pressure intensifier to a predetermined pressure and is then maintained at this pressure for a predetermined period of time.

The method and the device are especially suitable for use in high-pressure treatment of large quantities of liquid substances and where certain demands are placed on how large a volume of the substance that can be treated per unit of time.

BACKGROUND ART

In recent years, high-pressure treatment has started to be utilized as a method for, among other things, inactivating microorganisms and certain enzymes in foodstuffs, in particular in foodstuffs of a particularly high quality, such as fruit juices and the like. The advantage of high-pressure treatment as compared with the more frequently used heat-treatment method is that the microorganisms and the degrading enzymes in the freshly pressed juice are killed or inactivated without destroying vitamins and flavouring. During heat treatment, on the other hand, the taste and the vitamin contents are changed, which requires additives to restore, as far as possible, the nutritive value and taste of the freshly pressed juice.

A decisive factor for obtaining a good result during the high-pressure treatment is that the substance is maintained under a sufficiently high pressure for a sufficiently long period of time. The pressure and the holding time are chosen in dependence on the properties of the substance to be treated, and the general rule is that the higher the pressure and the longer the holding time, the better the result. Further, the rule applies, within certain limits, that if the holding time is extended, the pressure can be reduced and vice versa. During treatment of fruit juices, the pressure is usually set a 1,000–15,000 bar and the holding time can vary between a few seconds and some 10 to 30 minutes.

During high-pressure treatment of liquid substances, a so-called pressure intensifier is used. By pressure intensifier is meant here a device which has a high-pressure chamber in which the substance to be treated is pressurized. The pressurization can be accomplished, for example, by designing one of the end walls of the high-pressure chamber as a high-pressure piston with a certain area, which is insertable into the high-pressure chamber. Outside of the high-pressure chamber this piston is secured to a low-pressure piston with a larger area, arranged in a low-pressure chamber. By supplying a certain pressure to the low-pressure piston, for example hydraulically, a higher pressure is thus obtained inside the high-pressure chamber.

When liquid substances are to be treated by high pressure using the present technique, a quantity of the substance as large as can be contained in the pressure intensifier is supplied thereto. Thereafter, the substance is pressurized to the predetermined pressure and is kept in the pressure intensifier at this pressure for the predetermined period of time. After expiration of the predetermined holding time, the pressure in the pressure intensifier is reduced, whereby the substance is decompressed. When the decompression is completed, the substance is removed from the pressure intensifier and the high-pressure treatment is thereby completed.

During industrial manufacture of, for example, juice, but also of other liquid products, a process is often used in which all treatment steps from the raw material to the finished and packaged product are carried out in one unbroken chain. When high-pressure treatment is applied, the high-pressure treatment is thus included as one link in the process chain. According to the prior art as above, one or up to three pressure intensifiers are used in a process chain. In those cases where two or three pressure intensifiers are used, these can utilize one and the same hydraulic unit for generating the pressure by operating in parallel and with a certain mutual time delay.

Technical Problem

Since industrial manufacture of, for example, juice is carried out by means of a process, that treatment step in the process chain which has the lowest capacity with respect to the treated volume per unit of time becomes limiting to the production capacity of the whole process chain. This fact entails problems during high-pressure treatment using current technique as described above.

A considerable problem is that the volume of the pressure intensifier must be dimensioned in relation to the desired production capacity of the whole process chain. In addition to the high-pressure treatment, the packing process is often that part of the production chain that is limiting to the capacity of the whole process. Normal packing machines for juice today have a capacity of about 6,000 to 12,000 liters per hour. If high-pressure treatment is to have a capacity of 6,000 liters per hour and the predetermined holding time is 5 minutes at a suitable pressure, this means that the pressure intensifier must hold about 500 liters of juice. Further, since the pressure intensifier is to be able to generate extremely high pressures, the manufacturing cost of the pressure intensifier stated in the example is very high. From this follows that in order to maintain the necessary capacity in the high-pressure treatment, a pressure intensifier with a very high machine cost per hour is required. In addition, the pressure intensifier is idle for the most part of the high-pressure treatment, namely, during the whole holding time. This, of course, entails considerable economic disadvantages during high-pressure treatment using current technique.

By utilizing several pressure intensifiers in parallel, connected to one and the same hydraulic unit, the efficiency of the hydraulic unit can be increased somewhat. Still, the need of relatively large pressure intensifiers remains, as does the problem of the pressure intensifiers remaining idle during the holding time.

Further, the need of large pressure intensifiers entails problems as regards the energy consumption. To obtain an optimum capacity during the high-pressure treatment, the cycle times should be minimized. The holding time cannot be reduced unless the pressure is increased, which in turn entails further increased manufacturing costs for the pressure intensifier. Instead, the cycle times can be reduced by reducing the time of the pressurization step. When the pressure intensifier has a large volume, however, this means that the energy required for building up the pressure increases considerably. This in turn leads to high operating costs and to the need of powerful and expensive hydraulic units.

To keep cycle times low, it is important that the pressure intensifier be filled and emptied as quickly as possible. When the pressure intensifier has a large volume, this means pulsating flows with high rates of flow, which leads to fatigue stresses in high-pressure components, such as tubes, elbows and valves.

One further problem with high-pressure treatment according to the current technique resides in the fact that the large quantities of energy which are supplied to the substance during the pressurization cannot be recovered in a simple manner during the decompression of the substance. This, of course, entails higher operating costs than what would have been the case if simple recovery of the energy were possible.

The object of the present invention is, therefore, to provide a method and a device for high-pressure treatment of liquid substances whereby the volume of the pressure intensifier does not have to be dimensioned in relation to the desired treatment capacity and whereby it is possible, in a simple manner, to recover the energy which is supplied to the substance during pressurization of the substance.

The Solution

The above-mentioned object is attained according to the invention by means of a method of the kind stated in the introductory part of the description and characterized in that the limited amount of the substance, after having been pressurized in the pressure intensifier, is conducted while substantially maintaining the predetermined pressure from the pressure intensifier to and via an inlet into a pressure chamber, which contains a predetermined larger quantity of the substance at essentially the same predetermined pressure, and that the substance is maintained at the predetermined pressure for the predetermined time by being brought to pass over a predetermined distance between the inlet and an outlet arranged in the pressure chamber.

During high-pressure treatment according to the invention, the pressure intensifier can be dimensioned to generate a certain capacity flow independently of the required holding time. The attainment of the holding time is, at a certain capacity flow, exclusively dependent on the volume of the pressure chamber. Since the pressure intensifier therefore can be made considerably smaller than according to prior art and since pressure chambers are considerably less expensive to manufacture per unit of volume than pressure intensifiers, the above-mentioned economic and technical problems associated with a large volume of the pressure intensifier are eliminated.

According to a preferred embodiment of the method, the predetermined pressure in the pressure chamber is maintained essentially constant by passing a quantity of the substance from the pressure chamber through the outlet which is essentially equal to the quantity supplied to the pressure chamber through the inlet during the same cycle.

According to one embodiment of the invention, after having passed through the pressure chamber the substance is supplied to a decompressor, in which the supplied quantity of the substance is decompressed in a controlled way.

A further embodiment of the method according to the invention is characterized in that the pressure which is supported by the substance in the decompressor is transferred to the pressure intensifier and there contributes to the pressurization of the limited quantity of the substance which, during the decompression in the decompressor, is located in the pressure intensifier.

The latter embodiment of the invention permits the energy which is released in connection with the decompression of the substance to be recovered and used during the otherwise relatively energy-demanding pressurization. This entails a considerable reduction of the energy consumption compared with the high-pressure treatment according to the current technique.

According to two further embodiments of the invention, the released energy can be transferred from the decompressor either by hydraulic means or by mechanical means.

Further, the method according to one embodiment of the invention permits the substance, after having been conducted from the pressure chamber, to be brought to pass through at least one choke means, instead of being passed to the decompressor. Thereafter, according to an additional embodiment, the substance is caused, after preferably each choke means, to pass through a heat exchanger whereby the temperature of the substance is compensated for the change of temperature which arises when passing through the choke means.

These two latter embodiments permit, if desired, homogenization of the substance to be included as part of the high-pressure treatment and result in the temperature of the substance not being significantly influenced by this homogenization.

The present invention also relates to a device for carrying out the method according to the invention. The device comprises a pressure intensifier operating in a cyclic process and adapted, during each cycle, to pressurize a limited amount of the substance to be treated to the predetermined pressure, and is characterized in that a pressure chamber with an inlet and an outlet, via the inlet and a first high-pressure connection for transporting the pressurized substance, is connected to the pressure intensifier, that the pressure chamber is adapted to maintain the substance at the predetermined pressure during the predetermined period of time by a forced smallest transport distance between the inlet and the outlet, determined by the volume flow and the flow cross section, and that a valve is arranged to close and open the connection between the pressure intensifier and the pressure chamber.

According to two different embodiments, the pressure chamber can either be designed as a tube, whereby the length of the tube constitutes the forcedly determined smallest transport distance between the inlet and the outlet, or as a cylinder.

Further, the pressure chamber according to one embodiment is provided with guide means intended to cause the pressurized substance to cover the forcedly determined smallest distance between the inlet and the outlet. According to one embodiment, this guide means consists of a conduit of flexible material, one end of the conduit being connected to the inlet of the pressure chamber and the other end of the conduit being connected to the outlet of the pressure chamber. Further, according to this embodiment, the conduit has a certain length which corresponds to the forcedly determined smallest distance over which the substance is to pass between the inlet and the outlet. The pressure chamber is filled with a pressure-absorbing medium in which the conduit is embedded. According to another embodiment, the guide means is in the form of a screw which is arranged coaxially with the pressure chamber and which has essentially the same outer diameter as the inner diameter of the pressure chamber. Further, according to still another embodiment, this screw is fixed to a shaft which is coaxial with the pressure chamber and the screw, the shaft being rotatably arranged at the two end walls of the pressure chamber and projecting through at least one of these end walls.

With the aid of the guide means according to the above, the pressurized substance is caused to pass over a certain predetermined distance in the pressure chamber. In this way it is ensured that the substance resides in the pressure chamber for the predetermined holding time. The different embodiments of the guide means all make possible a safe use as well as a simple cleaning and washing-up of the pressure chamber with guide means. In the embodiment with a flexible conduit, the washing-up takes place by flushing washing-up liquid and then rinsing liquid through the conduit, via the inlet and the outlet of the pressure chamber. When a rotatable screw is used as guide means, the washing-up takes place by first filling the pressure chamber with washing-up liquid to a certain level. Then, the screw is caused to rotate by rotating the shaft projecting from the pressure chamber, for example by means of a motor. This causes the washing-up liquid to be rinsed around in the pressure chamber and clean the guide means as well as the inside of the pressure chamber. After washing-up, the pressure chamber is rinsed in the same way with a rinsing liquid.

Yet another embodiment of the invention according to the invention is characterized in that the pressure chamber, via the outlet and a second high-pressure connection for transporting the pressurized substance, is connected to a decompressor, and that a second valve is adapted to close and open the connection between the pressure chamber and the decompressor.

With this embodiment, the substance is allowed to be decompressed in a controlled manner and undesired homogenization of the substance is thus avoided.

According to one embodiment, the two high-pressure connections consist of straight high-pressure tubes. This means a considerable advantage since cross-bores and other geometries, which are disadvantageous in a high-pressure context, are avoided.

According to one embodiment, the decompressor is provided with means for utilizing the pressure which is supported by the substance in the decompressor, these means communicating with pressure-generating means in the pressure intensifier.

This latter embodiment permits the energy which is released in connection with the decompression of the substance to be recovered and used for the otherwise relatively energy-demanding pressurization. This entails a considerable reduction of the energy consumption compared with high-pressure treatment according to the current technique.

Still another embodiment of the device according to the invention is characterized in that the pressure intensifier comprises a first high-pressure chamber for containing the substance to be pressurized, a first high-pressure piston which is displaceable in the first high-pressure chamber and has a first high-pressure area, a first low-pressure chamber for containing a pressure medium, a first low-pressure piston which is displaceable in the first low-pressure chamber and which is fixed to the first high-pressure piston and has a first low-pressure area which is larger than the first high-pressure area, and that the decompressor comprises a second high-pressure chamber for containing the pressurized substance, a second high-pressure piston which is displaceable in the second high-pressure chamber and has a second high-pressure area, a second low-pressure chamber for containing a pressure medium, and a low-pressure piston which is displaceable in this second low-pressure chamber and is secured to the second high-pressure piston and has a second low-pressure area which is larger than the second high-pressure area.

Still another embodiment is characterized in that the means for utilizing the pressure which is supported by the substance in the decompressor comprises the second high-pressure piston, the second low-pressure chamber and the second low-pressure piston, that the pressure-generating means comprise the first high-pressure piston, the first low-pressure chamber and the first low-pressure piston.

By combining the latter embodiments described above, several different possibilities are afforded to recover the energy which is released in connection with the decompression. One such possibility is represented by an embodiment of the invention which is characterized in that the first low-pressure chamber and the second low-pressure chamber consist of a common low-pressure chamber, and that the first low-pressure piston and the second low-pressure piston consist of a common low-pressure piston, the first and second high-pressure pistons being arranged on different sides of this common low-pressure piston.

With the embodiment mentioned above, the pressure which is supported by the substance in the decompressor is transmitted mechanically from the decompressor to the pressure intensifier. When the substance in the decompressor expands, the second high-pressure piston is displaced, whereby also the common low-pressure piston and the first high-pressure piston are displaced. The displacement of the first high-pressure piston thereby contributes to the pressurization of the substance in the high-pressure chamber of the pressure intensifier. If the first and second high-pressure areas are the same, the decompression and the pressurization will proceed until the pressure difference between the pressure of the substance in the decompressor and the pressure of the substance in the pressure intensifier has practically disappeared. For the substance in the pressure intensifier to attain the predetermined pressure, additional pressure must be supplied to the first high-pressure piston. This can be achieved by hydraulically pressurizing the pressure medium in the common low-pressure chamber, on that side of the common low-pressure piston which is opposite to the first high-pressure piston. However, a further embodiment of the invention is characterized in that the first high-pressure area is smaller than the second high-pressure area. In this way, the decompression of the substance in the decompressor results in a higher pressure of the substance in the pressure intensifier. Only a slight additional pressure need to be added to the low-pressure piston to overcome any friction losses. This embodiment thus offers a simple solution to the energy recovery problem during high-pressure treatment.

Another possibility of transmitting the pressure which is supported by the substance in the decompressor is afforded by an embodiment which is characterized in that the first low-pressure chamber is hydraulically connected to the second low-pressure chamber. The pressure intensifier and the decompressor are thus separated but they communicate hydraulically via their respective low-pressure chambers. In the same way as in the embodiment with mechanical transmission of pressure, the predetermined pressure in the decompressor can be caused to contribute to the pressurization of the substance in the pressure intensifier. This is achieved in one embodiment in that the first high-pressure area is smaller than the second high-pressure area and in another embodiment in that the first low-pressure area is larger than the second low-pressure area. The last two embodiments have the advantage that they allow the use of a small and inexpensive hydraulic pump for generating the last pressure increase up to the predetermined pressure.

BRIEF DESCRIPTION OF THE DRAWINGS

The exemplified embodiments of the invention will be described below with reference to the accompanying drawings, wherein.

Figure 1:
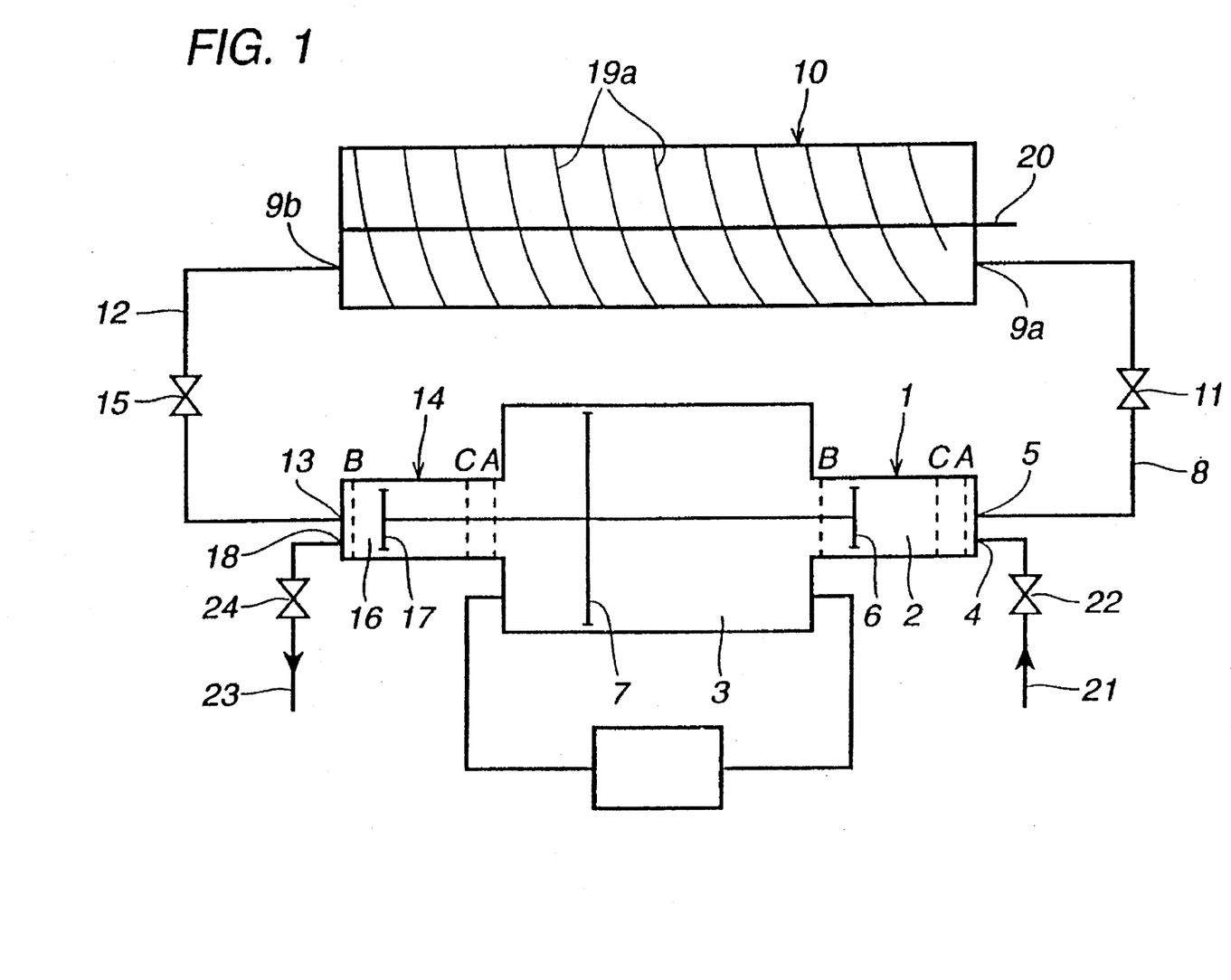
FIG. 1 is a schematic view of the method and the device according to one embodiment of the invention.

The device for high-pressure treatment of liquid substances shown in FIG. 1 comprises a pressure intensifier 1 which has a high-pressure chamber 2 for containing the substance to be pressurized, and a low-pressure chamber 3 to contain hydraulic fluid. The high-pressure chamber 2 is provided with a first inlet 4 and a first outlet 5 for supply and discharge, respectively, of the substance to be treated. Further, in the high-pressure chamber 2 a first high-pressure piston 6 with a first high-pressure area is displaceably arranged. The first high-pressure piston 6 is secured to a low-pressure piston 7 which has a first low-pressure area and which is displaceably arranged in the low-pressure chamber 3. The first low-pressure area is larger than the first high-pressure area, which means that if the hydraulic fluid in the low-pressure chamber 3 is pressurized to a certain pressure, this results in a higher pressure of the substance in the high-pressure chamber 2. The above is within the scope of the prior art.

Further, the device according to the invention comprises a first high-pressure connection 8 which connects the first outlet 5 on the pressure intensifier 1 to a second inlet 9a on a cylindrically shaped pressure chamber 10. On this first high-pressure connection 8 a first valve 11 is arranged, which valve 11 makes possible opening and closing of the connection between the pressure intensifier 1 and the pressure chamber 10. This valve need not be placed on the high-pressure connection 8, but can also be arranged, for example, inside the pressure chamber 10 adjacent to the second inlet 9a, or inside the high-pressure chamber 2 of the pressure intensifier 1 adjacent to the first outlet 5. Further, the pressure chamber 10 is provided with a second outlet 9b which, via a second high-pressure connection 12, communicates with a third inlet 13 on a decompressor 14. This second high-pressure connection 12 is provided with a second valve 15, which makes possible closing of the connection between the pressure chamber 10 and the decompressor 14. In a manner analogous to the first valve 11, this second valve 15 need not be arranged exactly on the high-pressure connection 12. The decompressor comprises a second high-pressure chamber 16 in which a second high-pressure piston 17 is displaceable arranged. This second high-pressure piston 17, which has a second high-pressure area, is secured to the low-pressure piston 7 of the pressure intensifier 1. The decompressor 14 and the pressure intensifier 1 thus have a common low-pressure chamber 3 and low-pressure piston 7. Further, the decompressor 14 is provided with a third outlet 18 from the second high-pressure chamber 16.

The areas of the two high-pressure pistons 6, 17 are so shaped that the first high-pressure area is smaller than the second high-pressure area.

In the pressure chamber 10, a screw 19a is arranged coaxially with the pressure chamber 10. This screw 19a is secured to a shaft 20, which shaft 20 is coaxial with the pressure chamber 10 and rotatably arranged in the two end walls of the pressure chamber. Further, the shaft 20 is so arranged that at least one of its ends extends out through the end wall of the pressure chamber 10.

The device is connected to the rest of the manufacturing chain through an inflow conduit 21 which has an inflow valve, and an outflow conduit 23 which has an outflow valve 24.

In the following, the embodiment of the method for high-pressure treatment of liquid substances according to the invention, shown in FIG. 1, will be described.

At the start of a treatment cycle, the first high-pressure piston 6 is in a fully inserted position and the second high-pressure piston 17 is in a fully retracted position. These positions are shown in dashed lines and have the designation A in FIG. 1. The first high-pressure chamber 2 is empty and the second high-pressure chamber 16 is filled with newly decompressed liquid. Further, the valves 11 and 15 are closed as are the inflow and outflow valves 22 and 24, respectively.

A cycle starts by opening of the inflow valve 22 and the outflow valve 24. Thereafter, the low-pressure piston 7 is caused hydraulically to be displaced to the left in the figure. The two high-pressure pistons 6 and 17 are thus displaced to their respective positions B. This causes the second high-pressure chamber 16 to become emptied through the outflow conduit 23. At the same time, a predetermined amount of the substance to be subjected to treatment by pressure is supplied via the inflow conduit 21 to the first high-pressure chamber 2. The supply can be brought about, for example, by an ordinary low-pressure pump (not shown). The magnitude of the supplied amount of the substance is determined by the stroke volume of the pressure intensifier 1 and may, in the exemplified case, be about 20 to 30 liters.

When the pressure intensifier 1 is filled and the decompressor 14 is emptied, the inflow and outflow valves 22 and 24, respectively, are closed. Thereafter, the valve 15 is opened, whereby the pressure prevailing in the pressure chamber 10 will act on the second high-pressure piston 17. In the example shown, the pressure in the pressure chamber 10 may be about 4,000 bar. Since the second high-pressure piston 17 is secured to the first high-pressure piston 6, a pressure balance between the first and second high-pressure chambers 2 and 16, respectively, will arise. The substance in the first high-pressure chamber 2 is thereby pressurized to the same pressure which prevails in the pressure chamber 10, which pressure corresponds to the predetermined pressure. To overcome the friction upon pressure equalization between the first and second pressure chambers 2 and 16, respectively, the second high-pressure area of the second high-pressure piston 17 is larger than the first high-pressure area of the first high-pressure piston 6.

When the pressure in the first high-pressure chamber 2 has reached the predetermined pressure, the valve 11 is opened. Then, the low-pressure piston 7 is caused hydraulically to become displaced to the right. The two high-pressure pistons 6 and 17 are thereby brought to their respective positions C in the figure. These positions C are so placed that the distances AC in the example shown corresponds to about 10–15% of the distances AB, whereby the distances AB constitute the piston stroke of the respective high-pressure pistons 6 and 17. The distance AC can vary for treatment of various substances and the distance is chosen in dependence on the degree of compression of the treated substance. When the two high-pressure pistons 6 and 17 are moved from position B to position C, a certain amount of the substance in the first high-pressure chamber 2 is moved via the first outlet 5, the first high-pressure connection 8, and the second inlet 9a into the pressure chamber 10. At the same time, an essentially equally large amount of the substance is brought from the pressure chamber 10 via the second outlet 9b, the second high-pressure connection 12 and the third inlet 13 into the second high-pressure chamber 16. This causes the predetermined pressure to be essentially maintained in the first high-pressure chamber 2, the first high-pressure connection 8, the pressure chamber 10, the second high-pressure connection 12, and in the second high-pressure chamber 16.

When the two high-pressure pistons 6 and 17 have reached their respective positions C, the valve 15 is closed.

Then, the low-pressure piston 7 is caused hydraulically to become displaced the remaining distance to the right in the figure. This causes the two high-pressure pistons to become displaced to their respective initial positions A. During this displacement from position C to position A, the remaining amount of the substance in the first high-pressure chamber 2 will be discharged through the first outlet 5 and, via the first high-pressure connection 8 and the second inlet 9a, be conducted into the pressure chamber 10. At the same time, the amount of the substance which is located in the second high-pressure chamber 16 will be decompressed. The rate of the decompression can thereby be controlled by hydraulically controlling the movement of the low-pressure piston 7.

When the two high-pressure pistons 6 and 17 have reached their respective initial positions A, the first high-pressure chamber 2 is empty and the second high-pressure chamber 16 is filled with newly decompressed liquid. Thereby, the high-pressure treatment cycle is completed and a new amount of the substance can be supplied to the pressure intensifier 1 while discharging the decompressed amount from the decompressor 14.

As will be clear from the description above, the pressure intensifier 1 operates as a high-pressure pump, which during each cycle pumps a certain amount of the substance to be treated into the pressure chamber 10. The pressure chamber 10 is intended to ensure that each amount of the substance is maintained at the predetermined pressure during the predetermined holding time. From this follows that the volume of the pressure chamber 10 is dimensioned according to the desired treatment capacity measured in treated volume of liquid per unit of time and according to the desired holding time. Let it be assumed, for example, that the desired treatment capacity is 6,000 liters per hour and the predetermined holding time is 5 minutes. The flow through the pressure chamber 10 will then be 100 liters per minute, and for the substance to reside in the pressure chamber 10 for 5 minutes its volume shall be 500 liters.

To ensure that no partial amount of the substance in the pressure chamber 10 passes between the second inlet 9a and the second outlet 9b on the pressure chamber 10 in a shorter time than the predetermined holding time, the pressure chamber is provided with internal guide means 19. In the embodiment shown in FIG. 1, this guide means 19 is in the form of a screw 19a. This screw is coaxial with the pressure chamber 10 and has an essentially equally large outer diameter as the inner diameter of the pressure chamber. The substance which is supplied to the pressure chamber 10 through the second inlet 9a is thus forced to cover a distance which is determined by the geometry of the screw 19a. In this way it is ensured that no partial amount of the substance passes essentially more rapidly through the pressure chamber than what is required for achieving the predetermined holding time.

Further, the screw 19a is fixed to a shaft 20 which is coaxial with the pressure chamber 10. This shaft 20 is rotatably journalled in the two end walls of the pressure chamber 10 and extends out through one end wall. This design allows a simple washing-up of the pressure chamber 10. When the pressure chamber 10 is to be washed up, it is first emptied of its contents. Then, washing-up liquid is supplied, for example, through the second inlet 9a. When the pressure chamber 10 is filled with washing-up liquid to a certain level, the screw 19a is set in rotation. The rotation is accomplished, for example, by connecting a motor to that part of the shaft 20 which extends outside the pressure chamber 10. During the rotation of the screw 19a, the washing-up liquid is flushed around inside the pressure chamber 10, whereby the interior of the pressure chamber and its screw 19a with the shaft 20 are washed up. After washing-up, rinsing can take place in the same way, whereby the washing-up liquid is replaced by rinsing liquid.

With the aid of the method and the device according to the invention, the volume of the expensive pressure intensifier 1 can be dimensioned independently of the holding time. The volume of the pressure intensifier 1 is instead dimensioned depending on the treatment capacity and the pump frequency of the pressure intensifier. Let it be assumed, for example, that the desired treatment capacity as before is 6,000 liters per hour and that the pressure intensifier is to operate with 20 pump strokes per minute. The required volume of the pressure intensifier 1 is thus 5 liters. Such a pressure intensifier is considerably less expensive to manufacture than a pressure intensifier with the volume 500 liters, which would be necessary without the use of a separate pressure chamber.

Figure 2:
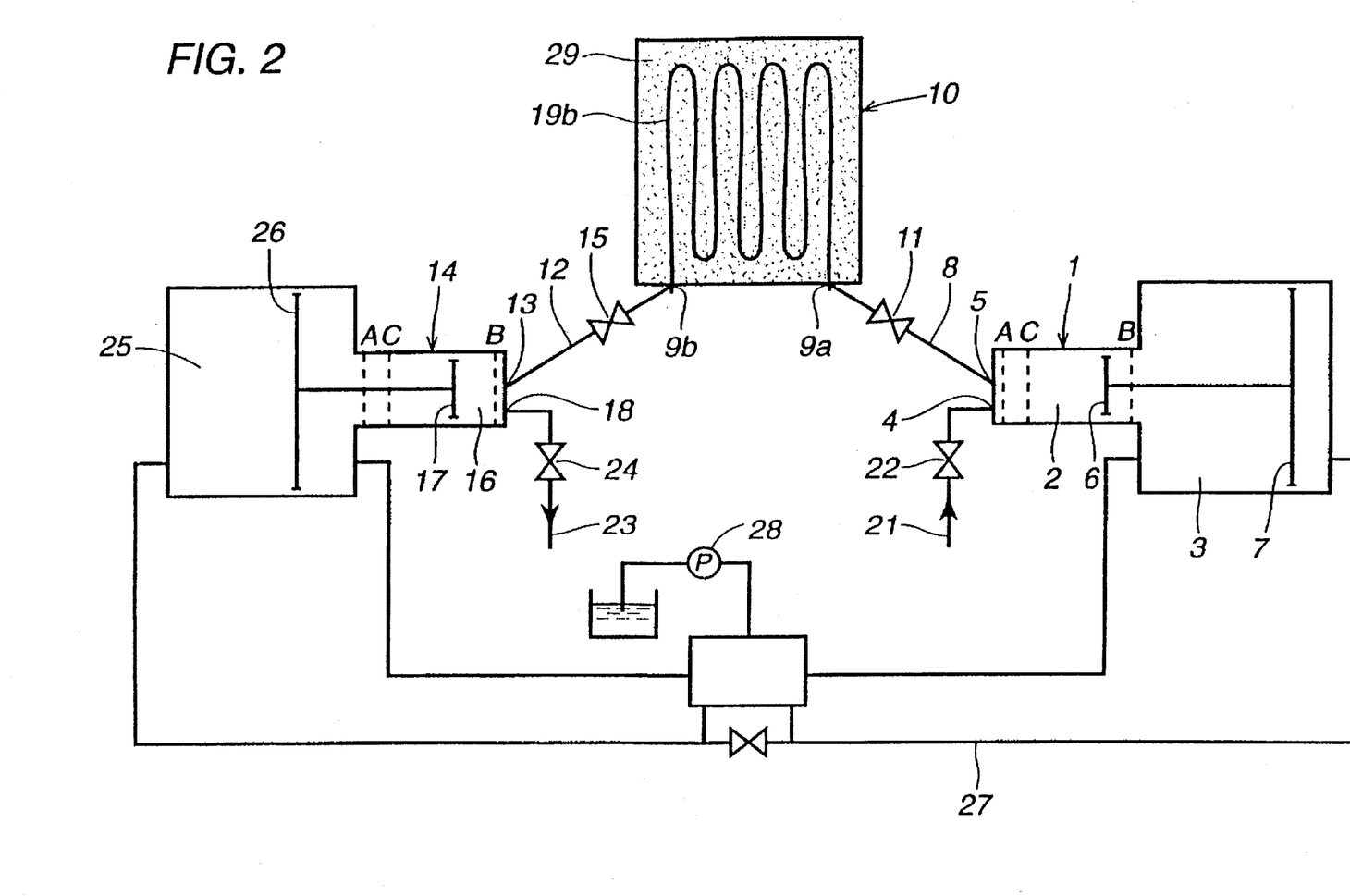
FIG. 2 is a schematic view of another embodiment of the method and the device according to the invention.

The embodiment of the device according to the invention shown in FIG. 2 comprises a pressure intensifier 1, a pressure chamber 10 and a decompressor 14. The pressure intensifier 1 and the decompressor are separated whereby the pressure intensifier 1 has a first low-pressure chamber 3 of its own, and in which the first low-pressure piston 7 is displaceably arranged. In similar manner, the decompressor has a second low-pressure chamber 25 of its own, in which a second low-pressure piston 26 is displaceably arranged. The first low-pressure piston 7 has a certain first low-pressure area, which is larger than a second low-pressure area of the second low-pressure piston. 26. The two low-pressure pistons 7, 26 are secured to their respective high-pressure pistons 6, 17. Further, the two low-pressure chambers 3, 25 are filled with a pressure medium and interconnected via a hydraulic line 27.

The embodiment of the method according to the invention shown in FIG. 2 differs from the embodiment shown in FIG. 1 in that the pressure which is supported by the substance in the decompressor 14 is transmitted to the pressure intensifier 1 via the hydraulic line 27. At the beginning of the decompression, the two high-pressure pistons 6 and 17 are in their respective positions B. The first high-pressure chamber 2 is filled with liquid which is to be pressurized. The valves 11 and 15 are closed, as are the inlet and outlet valves 22 and 24, respectively. When the valve 15 is opened, the pressure from the substance in the high-pressure connection 12 and in the pressure chamber 10 will act on the second high-pressure piston 17. Since this second high-pressure piston 17 is secured to the second low-pressure piston 26, also the pressure medium in the second low-pressure chamber 25 is pressurized. The pressure in the second low-pressure chamber 25 is transmitted via the hydraulic line 27, the first low-pressure chamber 3, the first low-pressure piston 7 and the first high-pressure piston 6 to the substance in the first high-pressure chamber 2. This results in a pressure balance between the first and second high-pressure chambers 2 and 16, respectively. The substance in the first high-pressure chamber 2 is thereby pressurized to the same pressure as that which prevails in the pressure chamber 10, which pressure corresponds to the predetermined pressure.

Thereafter, the valve 11 is opened and the two high-pressure pistons are caused to become displaced to their respective positions C. This is accomplished by a hydraulic pump 28 pumping additional pressure medium into the first low-pressure chamber 3. As the first low-pressure area is larger than the second low-pressure area, it is sufficient to use a relatively small and inexpensive hydraulic pump 28.

To obtain this advantage of making possible the use of a small hydraulic pump, it is also possible that the two low-pressure areas are equally large, but that the first high-pressure area is smaller than the second high-pressure area.

When the two high-pressure pistons 6 and 17 have been displaced to their respective positions C, the valve 15 is closed. Then the two high-pressure pistons are caused hydraulically to become displaced to their respective positions A, whereby the remaining amount of the substance in the pressure intensifier 1 is passed to the pressure chamber 10 while at the same time the substance in the decompressor 14 is decompressed.

In the embodiment of the device according to the invention shown in FIG. 2, the internal guide means of the pressure chamber 10 consists of a flexible hose 19b. This hose 19b is embedded in a pressure-absorbing medium 29 inside the pressure chamber 10. The hose 19b, which, for example, may be of teflon material, has a certain length which corresponds to the predetermined distance over which the substances is to pass in the pressure chamber 10 to reside in the pressure chamber 10 during the predetermined holding time. This embodiment of the internal guide means 19 gives a reliable solution which is easy to operate. During washing-up, for example, the two high-pressure connections 8 and 12 are detached from the pressure chamber 10, whereupon washing-up and rinsing liquid can be flushed through the hose 19b when it is still in the pressure chamber 10.

In the embodiment of the device according to the invention shown in FIG. 2, the two high-pressure contentions 8 and 12 further consist of straight high-pressure tubes. The fact that the high-pressure connections 8 and 12 are straight entails a considerable advantage, since cross-bores and bends or tube angles are thus avoided, which otherwise entail risks of leakage and fracture when exposed to high pressures.

Figure 3:
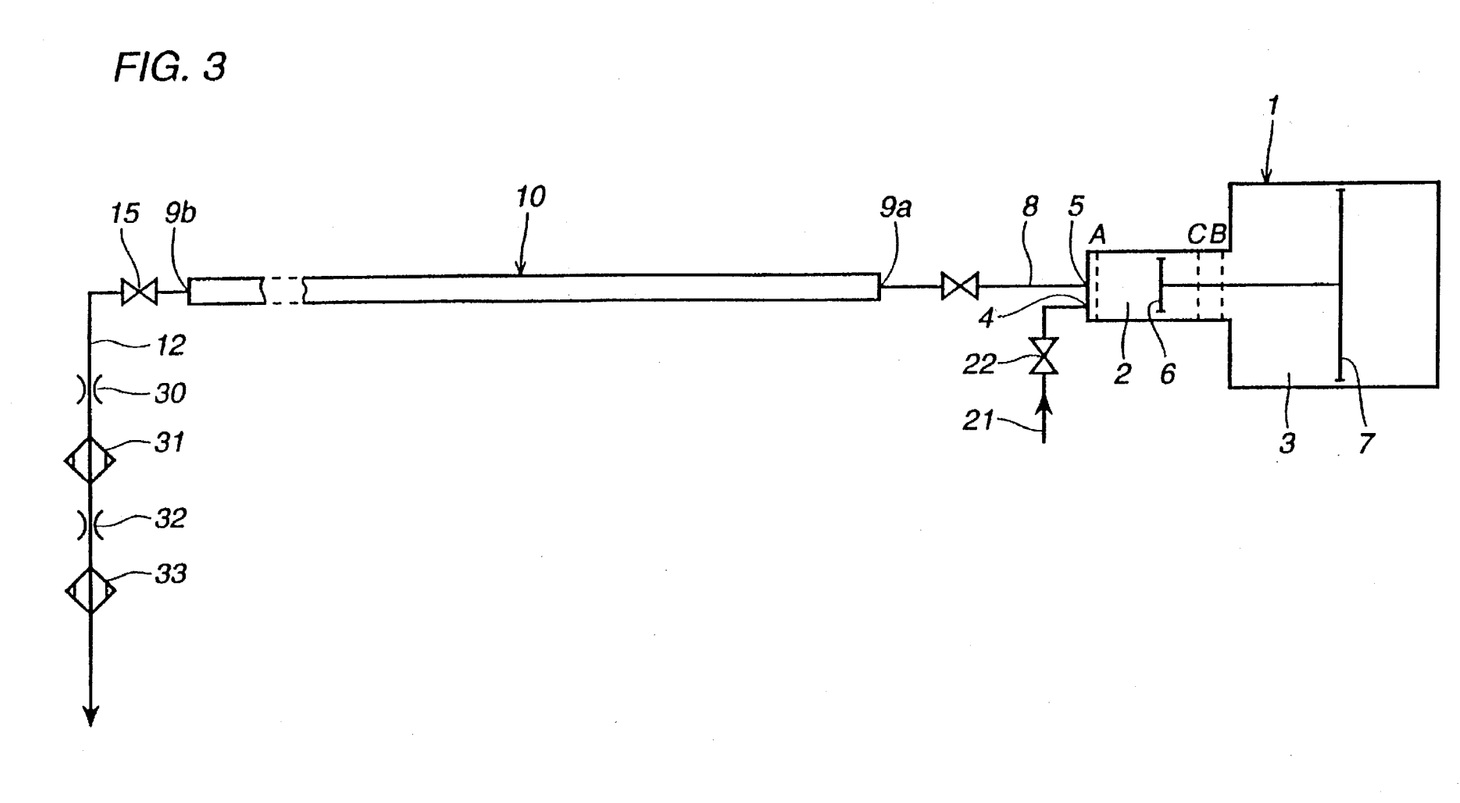
FIG. 3 is a schematic view of still another embodiment of the method and the device according to the invention.

The embodiment of the invention shown in FIG. 3 comprises a pressure intensifier 1, a pressure chamber 10 and means 30, 31, 32, 33 for homogenization of the substance subjected to pressure treatment. The pressure intensifier 1 acts as in the previously shown embodiments. The pressure chamber 10 is formed as an elongated tube, the length of the tube constituting the distance that the substance is to pass in order to reside in the pressure chamber 10 during the predetermined holding time. The second high-pressure connection 12 is connected to a first choke means 30, which is arranged close to a first heat exchanger 31. Further, a second choke means 32 with a heat exchanger 33 is connected to the first heat exchanger 31.

The above embodiment is used when the substance which is subjected to high-pressure treatment is also to be homogenized. The substance which leaves the pressure chamber 10 is conducted, while maintaining the pressure, to the first choke means 30. When the substance passes this choke means 30, the pressure is rapidly reduced whereby the substance is homogenized. Further, the temperature of the substance is increased in connection with the rapid change of pressure. After passage of the choke means 30, the substance is conducted to the heat exchanger 31 which essentially restores the temperature of the substance to the original one. After passage of the first choke means 30 and the heat exchanger 31, the substance is conducted to a second choke means 32 and a heat exchanger 33 whereby the pressure is reduced further with an ensuing compensation of the temperature. In the example shown, the homogenization takes place in two steps, but it is also possible to carry out the homogenization in one step or in more than two steps.

We claim:

1. A method for high-pressure treatment of a liquid substance, comprising the steps of:
    pressurizing a limited amount of the substance in a pressure intensifier to a predetermined pressure;
    maintaining the predetermined pressure for a predetermined time;
    conducting the limited amount of the substance, after the limited amount of substance has been pressurized in the pressure intensifier, while substantially maintaining the predetermined pressure, from the pressure intensifier into a pressure chamber via an inlet of the pressure chamber, the pressure chamber containing a predetermined larger amount of the substance at substantially the same predetermined pressure; and
    maintaining the substance at the predetermined pressure during the predetermined period of time by moving the substance over a predetermined distance between the inlet and an outlet of the pressure chamber (10).

2. A method according to claim 1, wherein the predetermined pressure in the pressure chamber is maintained substantially constant by moving an amount of the substance from the pressure chamber through the outlet which is substantially equal to the amount of the substance which is conducted into the pressure chamber through the inlet.

3. A method according to claim 1, further comprising the steps of supplying the amount of the substance which is passed from the pressure chamber to a decompressor, and decompressing the supplied mount of the substance in the decompressor in a controlled way.

4. A method according to claim 3, comprising the further step of transmitting pressure from the substance in the decompressor as it is decompressed to the pressure intensifier such that the transmitted pressure contributes to the pressurization of the limited amount of the substance which, during the decompression step, resides in the pressure intensifier.

5. A method according to claim 4, wherein the pressure is transmitted by hydraulic means.

6. A method according to claim 4, wherein the pressure is transmitted by mechanical means.

7. A method according to claim 1, comprising the further step of moving the substance, after moving the substance from the pressure chamber, through at least one choke means such that the substance is decompressed and homogenized.

8. A method according to claim 7, comprising the further step of moving the substance, after moving the substance through the choke means, through a heat exchanger.

9. A method according to claim 2, further comprising the steps of supplying the amount of the substance which is passed from the pressure chamber to a decompressor, and decompressing the supplied amount of the substance in the decompressor in a controlled way.

10. A method according to claim 2, comprising the further step of moving the substance, after moving the substance from the pressure chamber, through at least one choke means such that the substance is decompressed and homogenized.

11. The method according to claim 1, wherein the substance includes foodstuffs.

12. A device for high-pressure treatment of a liquid substance, comprising:
    a pressure intensifier for pressurizing a limited amount of the substance to a predetermined pressure;
    a pressure chamber, the pressure chamber having an inlet and an outlet, the pressure chamber being connected to the pressure intensifier through the inlet; and a first high-pressure connection for transport of the pressurized substance from the pressure intensifier to the inlet of the pressure chamber;

the pressure chamber including an outlet separated from the inlet by a transport distance, the substance being maintained at the predetermined pressure for a predetermined period of time by being moved between the inlet and the outlet, the predetermined time being a function of a volume flow of the substance and a flow cross section of the pressure chamber; and a valve disposed in the first high-pressure connection permitting opening and closing of the first high-pressure connection.

13. A device according to claim 12, wherein the pressure chamber is in the form of a tube, a length of the tube corresponding to the transport distance.

14. A device according to claim 12, wherein the pressure chamber is in the form of a cylinder.

15. A device according to claim 12, wherein the pressure chamber includes internal guide means for causing the pressurized substance to cover a smallest transport distance between the inlet and the outlet.

16. A device according to claim 15, wherein the guide means includes a conduit of flexible material, the conduit having a first end connected to the inlet of the pressure chamber and a second end connected to the outlet of the pressure chamber, the conduit having a length corresponding to the smallest transport distance between the inlet and the outlet, the pressure chamber including a pressure absorbing medium in which the conduit is embedded.

17. A device according to claim 15, wherein the guide means includes a screw arranged coaxially with the pressure chamber, the screw having an outer diameter and the pressure chamber having an inner diameter, the outer diameter of the screw being substantially the same as the inner diameter of the pressure chamber.

18. A device according to claim 17, further comprising a shaft, the screw being secured to the shaft, the shaft being coaxial with the pressure chamber and the screw, the shaft being rotatably journalled at end walls of the pressure chamber and extending outside the pressure chamber through at least one of the end walls of the pressure chamber.

19. A device according to claim 12, further comprising a decompressor, a second high-pressure connection, the pressure chamber being connected to the decompressor via the outlet and the second high-pressure connection, and a second valve arranged in the second high-pressure connection and permitting opening and closing of the second high-pressure connection.

20. A device according to claim 19, wherein the first high-pressure connection and the second high-pressure connection are in the form of straight high-pressure tubes.

21. A device according to claim 19, wherein the decompressor includes means for decompressing the substance, the decompressing means being in communication with pressure-generating means in the pressure intensifier.

22. A device according to claim 19, wherein the pressure intensifier includes a high-pressure chamber in which the limited amount of substance to be pressurized is contained, a first high-pressure piston displaceable in the high-pressure chamber and having a first high-pressure area, a first low-pressure chamber for containing a pressure medium, a first low-pressure piston displaceable in the first low-pressure chamber and being secured to the first high-pressure piston and having a first low-pressure area which is larger than the first high-pressure area, and wherein the decompressor includes a second high-pressure chamber in which the pressurized substance is contained, a second high-pressure piston displaceable in the second high-pressure chamber and having a second high-pressure area, a second low-pressure chamber for containing a pressure medium, and a low-pressure piston displaceable in the second low-pressure chamber and being secured to the second high-pressure piston and having a second low-pressure area which is larger than the second high-pressure area.

23. A device according to claim 14, wherein the pressure chamber includes internal guide means for causing the pressurized substance to cover a smallest transport distance between the inlet and the outlet.

24. A device according to claim 21, wherein the pressure intensifier includes a high-pressure chamber in which the limited amount of substance to be pressurized is contained, a first high-pressure piston displaceable in the high-pressure chamber and having a first high-pressure area, a first low-pressure chamber for containing a pressure medium, a first low-pressure piston displaceable in the first low-pressure chamber and being secured to the first high-pressure piston and having a first low-pressure area which is larger than the first high-pressure area, and wherein the decompressor includes a second high-pressure chamber in which the pressurized substance is contained, a second high-pressure piston displaceable in the second high-pressure chamber and having a second high-pressure area, a second low-pressure chamber for containing a pressure medium, and a low-pressure piston displaceable in the second low-pressure chamber and being secured to the second high-pressure piston and having a second low-pressure area which is larger than the second high-pressure area.

25. A device according to claim 24, wherein the decompressing means in the decompressor includes the second high-pressure piston, the second low-pressure chamber, and the second low-pressure piston, and wherein the pressure-generating means includes the first high-pressure piston, the first low-pressure chamber, and the first low-pressure piston.

26. A device according to claim 25, wherein the first low-pressure chamber and the second low-pressure chamber include a common low-pressure chamber, and wherein the first low-pressure piston and the second low-pressure piston include a common low-pressure piston, the first and second high-pressure pistons being arranged on one side each of the common low-pressure piston.

27. A device according to claim 26, wherein the first high-pressure area is smaller than the second high-pressure area.

28. A device according to claim 25, wherein the first low-pressure chamber is hydraulically connected to the second low-pressure chamber.

29. A device according to claim 28, wherein the first low-pressure area is larger than the second low-pressure area.

30. A device according to claim 29, wherein the first high-pressure area is smaller than the second high-pressure area.

* * * * *